(12) United States Patent
Gondo

(10) Patent No.: US 7,094,232 B2
(45) Date of Patent: Aug. 22, 2006

(54) ELECTRODE ROD FOR TREATING BIOLOGICAL TISSUE

(75) Inventor: Masakatsu Gondo, Shinjuku-ku (JP)

(73) Assignee: Kabushikikaisha Nihon M.D.M., (JP)

( * ) Notice: Subject to any disclaimer, the term of this patent is extended or adjusted under 35 U.S.C. 154(b) by 336 days.

(21) Appl. No.: 10/793,284

(22) Filed: Mar. 4, 2004

(65) Prior Publication Data

US 2004/0181213 A1    Sep. 16, 2004

(30) Foreign Application Priority Data

Mar. 11, 2003  (JP) .............................. 2003-065691

(51) Int. Cl.
*A61B 18/18*    (2006.01)
(52) U.S. Cl. .................... 606/41; 606/33; 606/45; 606/49
(58) Field of Classification Search .................. 606/41, 606/33
See application file for complete search history.

(56) References Cited

U.S. PATENT DOCUMENTS

| | | | |
|---|---|---|---|
| 4,517,975 A * | 5/1985 | Garito et al. ................. | 606/41 |
| 5,100,402 A * | 3/1992 | Fan ............................. | 606/41 |
| 5,195,959 A * | 3/1993 | Smith .......................... | 604/34 |
| 5,322,503 A * | 6/1994 | Desai .......................... | 604/21 |
| 5,364,393 A * | 11/1994 | Auth et al. ................... | 606/34 |
| 6,162,219 A * | 12/2000 | Nilsson et al. ................ | 606/41 |
| 6,447,510 B1 * | 9/2002 | Ellman et al. ................ | 606/45 |
| 2003/0109864 A1 * | 6/2003 | Greep et al. ................. | 606/41 |
| 2004/0153055 A1 * | 8/2004 | Allen et al. ................... | 606/41 |

* cited by examiner

*Primary Examiner*—Michael Peffley
*Assistant Examiner*—Alex Toy
(74) *Attorney, Agent, or Firm*—Adams & Wilks

(57) ABSTRACT

An electrode rod for treating a biological tissue is provided to properly carry out a surgical operation wherein a sufficient thermal shield is applied onto a core wire connected to an electrode at the root of the electrode. A heat resisting ceramic or polyimide non-metallic short tube 15 is loosely mounted onto the outer periphery of a small diameter metal core wire 14 (diameter, 0.7 mm or so) connected to an electromagnetic wave irradiating electrode 13 such that it covers the short tube at the root of the electrode 13. The short tube 15 is fixed by a heat resisting coating layer 16 made of tetrafluoroethylene or the like. A rod-shaped rigid metal core wire 14a having a relatively larger diameter is connected in a unified form to the small diameter metal core wire 14 and a heat resisting coating layer 16a is also applied onto the core wire 14a.

14 Claims, 5 Drawing Sheets

ELECTRODE ROD FOR TREATING BIOLOGICAL TISSUE

BACKGROUND OF THE INVENTION

1. Field of the Invention

The present invention relates to a biological tissue treating device, in which the treatment of the biological tissue, such as dissipation due to vaporization, incision, excision, coagulation and arresting of bleeding, is carried out in an electromagnetic field proximate to the tissue in the action of an electromagnetic energy of the electromagnetic field emanating from the tip of an electrode for irradiating an electromagnetic field, and more specifically to an electrode rod for treating a biological tissue, which rod is equipped with such an electrode for irradiating an electromagnetic wave.

2. Description of the Related Art

Generally, as shown in FIG. 8, a biological tissue treating device equipped with an electromagnetic electrode includes a high frequency power supply 1 for generating a high frequency current having a radio frequency of, for example, 8 MHz–60 MHz in a wide band, and the high frequency current generated by the high frequency power supply 1 is supplied to an electromagnetic wave irradiating electrode 5 via an impedance matching unit 3 and a high frequency current cable 11.

The high frequency current cable 11 comprises a core wire 2 and a shield tube 6, which coaxially surrounds the core wire 2 via an insulating material. The proximal end of the core wire 2 is connected to terminal 7a for one electrode of the high frequency power supply 1 via the matching unit 3, and the proximal end of the shield tube 6 is connected to terminal 7b for the other electrode of the HF power supply 1 via both the matching unit 3 and a lead wire 7. The electromagnetic wave irradiating electrode 5 can be mounted at one end of a removable core wire 2a connected to the distal end of the core wire 2 via a socket 11a.

In FIG. 8, moreover, reference numerals 8, 9 and 10 mean a biological tissue, a local area thereof and a portion to be irradiated by the electromagnetic wave, respectively.

As shown in FIGS. 9 and 10, the conventional electrode rod for treating a biological tissue, which electrode rode includes an electromagnetic wave irradiating electrode 5 and a core wire 2a, is connected to a stainless steel electrode 5, and a heat resisting coating layer 12 is applied onto an conductor area extending from a flexible metal core wire 2a having a relatively small diameter to a rigid metal rod core wire 2b having a relatively large diameter. Since the electrode 5 is normally operated at an extremely high temperature (about 200° C.), the tip 12a of the insulation layer 12 is disposed away from the electrode 5 by a distance of several millimeters in order to avoid the burning up. Accordingly, such an exposed core wire 2a resides in the vicinity of the electrode 5 in the conventional electrode rod, and therefore the surface of such an exposed section becomes to be at a high temperature in the operation state. In this case, there is a possibility that a local portion other than that not to be treated in the biological tissue becomes into contact with the exposed section of the core wire, and then burns out, thus causing a disadvantage to be provided, since great skill is required in the operation of the electrode rod.

SUMMARY OF THE INVENTION

Accordingly, it is an object of the present invention to provide an electrode for treating a biological tissue, with the aid of which a proper surgical operation can be performed by providing a sufficient thermal insulation or shield at the root of the electromagnetic wave irradiating electrode connected to the core wire.

The above object of the present invention is attained by the following measures:

In accordance with the invention, an electrode rod for treating a biological tissue comprises an electromagnetic wave irradiating electrode; a small diameter metal core wire, said electromagnetic wave irradiating electrode is connected at the tip thereof, said small diameter metal core wire being capable of being used in a predetermined bent shape; a heat resisting non-metallic short tube loosely mounted onto the outer periphery of said small diameter metal core wire so as to cover the root of said electromagnetic wave irradiating electrode; a first heat resisting coating layer coating the outer periphery of said short tube at the distal end thereof with respect to said electromagnetic wave irradiating electrode and onto the outer periphery of said small diameter metal core wire to fix said short tube; a rod-shaped rigid metal core wire having a relatively larger diameter, said rigid metal core wire being connected to said small diameter metal core wire in a unified shape; and a second heat resisting coating layer connected in a unified form to said first heat resisting coating layer and coating the outer periphery of said rod-shaped rigid metal core wire, except, the outer periphery of a metallic surface for inserting into a socket at the proximal end.

In each of the electrode rods for treating a biological tissue according to the invention, the heat resisting non-metallic short tube which is mounted onto the outer periphery of the small diameter metal core wire connected to the electromagnetic wave irradiating electrode covers the root of the electromagnetic wave irradiating electrode at the tip of the core wire, so that the core wire is not exposed to the electrode at an extremely high temperature in the operation state. As a result, the treatment of the tissue, such as incision or the like, using the electrode is properly carried out.

In this case, the heat resisting non-metallic short tube is loosely mounted on the small diameter core wire, so that no crack occurs in the short tube, even if the diameter of the core wire increases due to the thermal expansion. In addition, since the short tube is fixed by the heat resisting coating layer on the core wire, any movement of the short tube is suppressed.

Moreover, a surgeon is able to bend such a small diameter core wire, thereby enabling a proper treatment to be carried out in accordance with the shape of the diseased part of the biological tissue.

Hence, the treatment of the tissue is carried out with the aid of the electromagnetic wave irradiating electrode in the state of operation. A specific feature of the electrode rod for treating a biological tissue according to the invention is that the electromagnetic wave irradiating electrode is formed in the shape of a ball, and therefore is optimally used for evaporating the biological tissue. The contact of the ball-shaped electrode with the biological tissue in a larger area causes the tissue to be gradually dissipated due to the evaporation, so that the coagulation area due to the thermal conduction is increased, thereby making it possible to enhance the ability for arresting of bleeding.

Moreover, another specific feature of the electrode rod for treating a biological tissue according to the invention is that the electromagnetic wave irradiating electrode is formed in the shape of a needle, and therefore can be optimally used to incise the biological tissue. In this case, the contact area of the electrode with the biological tissue is smaller, so that the heat diffusion in the tissue is restricted, and therefore a sharp incision can be carried out. As a result, the dissipation of the tissue due to evaporation is attained, using the tip of the needle, at a restricted area in the vicinity of a nerve or the like where the dissipation of heat had to be suppressed.

Moreover, another specific feature of the electrode rod for treating a biological tissue according to the invention is that the electromagnetic wave irradiating electrode is formed in the shape of a blade. In this case, the contact area of the electrode with the biological tissue is greatly increased so that it is optimally used to perform the incision accompanied with the coagulation due to the thermal conduction.

Moreover, another specific feature of the electrode rod for treating a biological tissue according to the invention is that the electromagnetic wave irradiating electrode is formed in the shape of a ring, and therefore it can be effectively used for excising a biological tissue providing a relatively small amount of bleeding at a wider area. In this case, the contact area of the electrode with the biological tissue is restricted, thereby enabling the thermal coagulation to be reduced.

Moreover, another specific feature of the electrode rod for treating a biological tissue according to the invention is that the electromagnetic wave irradiating electrode is formed in the shape of a sickle, thereby making it possible to excise the biological tissue at a wider area, as similarly to the case of the ring-shaped electrode. However, a relatively larger contact area of the electrode with the biological tissue allows the thermal coagulation to take place to some extent, and the dissipation due to the evaporation in the curved surface can also be carried out with the curved area at the tip of the electrode.

Moreover, another specific feature of the electrode rod for treating a biological tissue according to the invention is that the electromagnetic wave irradiating electrode is formed in the shape of a knife. In this case, the advantage resulting from the needle-shaped electrode and that resulting from the blade-shaped electrode can be obtained by the electrode.

Moreover, another specific feature of the electrode rod for treating a biological tissue according to the invention is that the diameter of the small diameter metal core wire is 0.7 mm, the length and the outside diameter of the heat resisting non-metallic short tube are 3 mm and 1.1 mm, respectively, and the heat resisting coating layer is produced from tetrafluoroethylene.

A surgeon can properly operate the diseased part of a patient with the electrode rod for treating a biological tissue according to the invention, where the electrode rod has the above-mentioned sizes and is produced from the above-mentioned material, by selecting the diameter of the small diameter metal core wire or the like and by bending the small diameter metal core wire in accordance with the shape of the diseased part.

Moreover, another specific feature of the electrode rod for treating a biological tissue according to the invention is that the material of the heat resisting non-metallic short tube is ceramic. As a result, the metal core wire connected to the electrode at the root is thermally shielded in a proper manner, thereby making it possible to carry out the treatment of the biological tissues such as incision or the like with the electrode itself.

Moreover, another specific feature of the electrode rod for treating a biological tissue according to the invention is that the material of the heat resisting non-metallic short tube is polyimide. The heat resisting property of polyimide provides not only an effect similar to that in the case of ceramic, but also a workability of machining with a reduced cost due to the plastic property of polyimide.

DESCRIPTION OF THE PREFERRED EMBODIMENTS

Referring now to the accompanying drawings, the preferred embodiments of the invention will be described.

Figure 1:
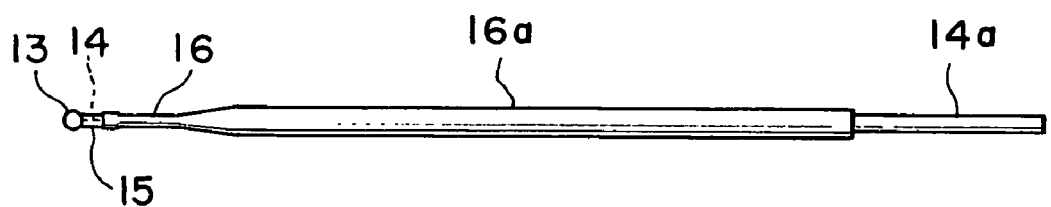
FIG. 1 is a side view of an electrode rod for treating a biological tissue in a first embodiment of the invention.
Figure 2:
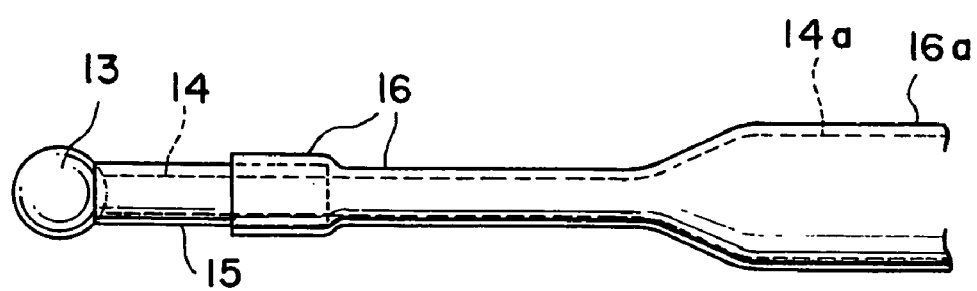
FIG. 2 is an enlarged side view of the tip of the electrode rod in FIG. 1.

In an electrode rod for treating a biological tissue according to a first embodiment of the invention, as shown in FIGS. 1 and 2, a flexible metal core wire 14 having a small diameter (diameter 0.7 mm) is equipped with a ball-shaped electromagnetic wave irradiating electrode 13 which has a stainless steel ball (diameter 1–2 mm) at the tip, and a heat resisting non-metallic short tube 15 (length 3 mm–1.1 mm) is loosely mounted on the outer periphery of the core wire 14 such that it covers the root of the electrode 13. The material of the short tube 15 is either ceramic or polyimide.

Moreover, a heat resisting coating layer 16 for fixing the short tube 15 covers the outer periphery of the flexible metal core wire 14 such that it covers the short tube 15 at the distal end thereof with respect to the electrode 13.

Similarly, onto a rigid metal rod shaped core wire 14a having a relatively large diameter, which is connected in a unified form to the flexible metal core wire 14, a heat resisting coating layer 16a connected in a unified form to the coating layer 16 is applied such that the outer peripheral surface of a metal for inserting a socket is exposed in the proximal end.

As for the heat resisting material for the coating layers 16 and 16a, a fluorine compound such as tetrafluoroethylene (poly-tetrafluoroethylene) is preferably used.

In the electrode rod for treating a biological tissue according the first embodiment, the heat resisting non-metallic short tube 15 mounted onto the periphery of the small diameter metal core wire 14 connected to the electromagnetic wave irradiating electrode 13 covers the root of the electromagnetic electrode 13 in the tip of the core wire 14, thereby enabling the core wire 14 to be prevented from exposing to the electrode 13 at an extremely high temperature in the operation state. As a result, the treatment of the biological tissue, such as incision or the like, can be optimally carried out, using the electrode 13.

Since the heat resisting short tube 15 is loosely mounted onto the core wire 14 having a small diameter, no crack appears in the short tube 15, even if the diameter of the core wire 14 is increased due to the thermal expansion. Since, moreover, the short tube 15 is fixed by the heat resisting coating layer 16 on the core wire 14, any movement of the short tube 15 is suppressed.

The small diameter metal core wire 14 can be bent for the sake of ease in operation by a surgeon, and therefore an optimal treatment can be carried out in accordance with the shape of the biological tissue.

As described above, the treatment of the biological tissue is carried out, using the electromagnetic wave irradiating electrode in the operation state. Since, moreover, the electrode rod for treating a biological tissue according to the first embodiment has a ball-shaped electrode 13, it is optimally used to dissipate the biological tissue by the evaporation. In this case, the ball-shaped electrode 13 is in contact with the biological tissue in a larger area, and the dissipation due to the evaporation gradually takes place, so that the coagulation area due to the thermal conduction becomes larger, and therefore the ability of arresting of the bleeding is enhanced.

Figure 3:
FIG. 3 is a side view of an electrode rod for treating a biological tissue in a second embodiment of the invention.

In a second embodiment of the invention, an electromagnetic wave irradiating electrode 13a is formed in the shape of a needle, as shown in FIG. 3. Accordingly, it can be optimally used to incise a biological tissue. In this case, the contact area of the electrode 13a with the biological tissue is smaller, so that the heat diffusion in the tissue is restricted, and therefore a sharp incision can be carried out. As a result, the dissipation of the tissue due to evaporation is attained, using the tip of the needle, at a restricted area in the vicinity of a nerve or the like where the dissipation of heat had to be suppressed.

Figure 4:
FIG. 4 is a side view of an electrode rod for treating a biological tissue in a third embodiment of the invention.

In a third embodiment of the invention, an electromagnetic wave irradiating electrode 13b is formed in the shape of a blade, as shown in FIG. 4. In this case, the contact area of the electrode 13b with the biological tissue is greatly increased so that it is optimally used to perform the incision accompanied with the coagulation due to the thermal conduction.

Figure 5:
FIG. 5 is a side view of an electrode rod for treating a biological tissue in a fourth embodiment of the invention.

In a fourth embodiment of the invention, an electromagnetic wave irradiating electrode 13c is formed in the shape of a ring, as shown in FIG. 5. As a result, it can be optimally used to excise a biological tissue providing a relatively small amount of bleeding at a wider area. In this case, the contact area of the electrode 13c with the biological tissue is relatively small and therefore the thermal coagulation takes place in a small area.

Figure 6:
FIG. 6 is a side view of an electrode rod for treating a biological tissue in a fifth embodiment of the invention.

In a fifth embodiment of the invention, an electromagnetic wave irradiating electrode 13d is formed in the shape of a sickle, as shown in FIG. 6. It can be used to excise a biological tissue at a wider area, as similarly to the case of the ring-shaped electrode 13c. However, a relatively larger contact area of the electrode 13d with the biological tissue allows the thermal coagulation to take place to some extent, and the dissipation due to the evaporation in the curved surface can also be carried out with the curved area at the tip of the electrode 13d.

Figure 7:
FIG. 7 is a side view of an electrode rod for treating a biological tissue in a sixth embodiment of the invention.
Figure 8:
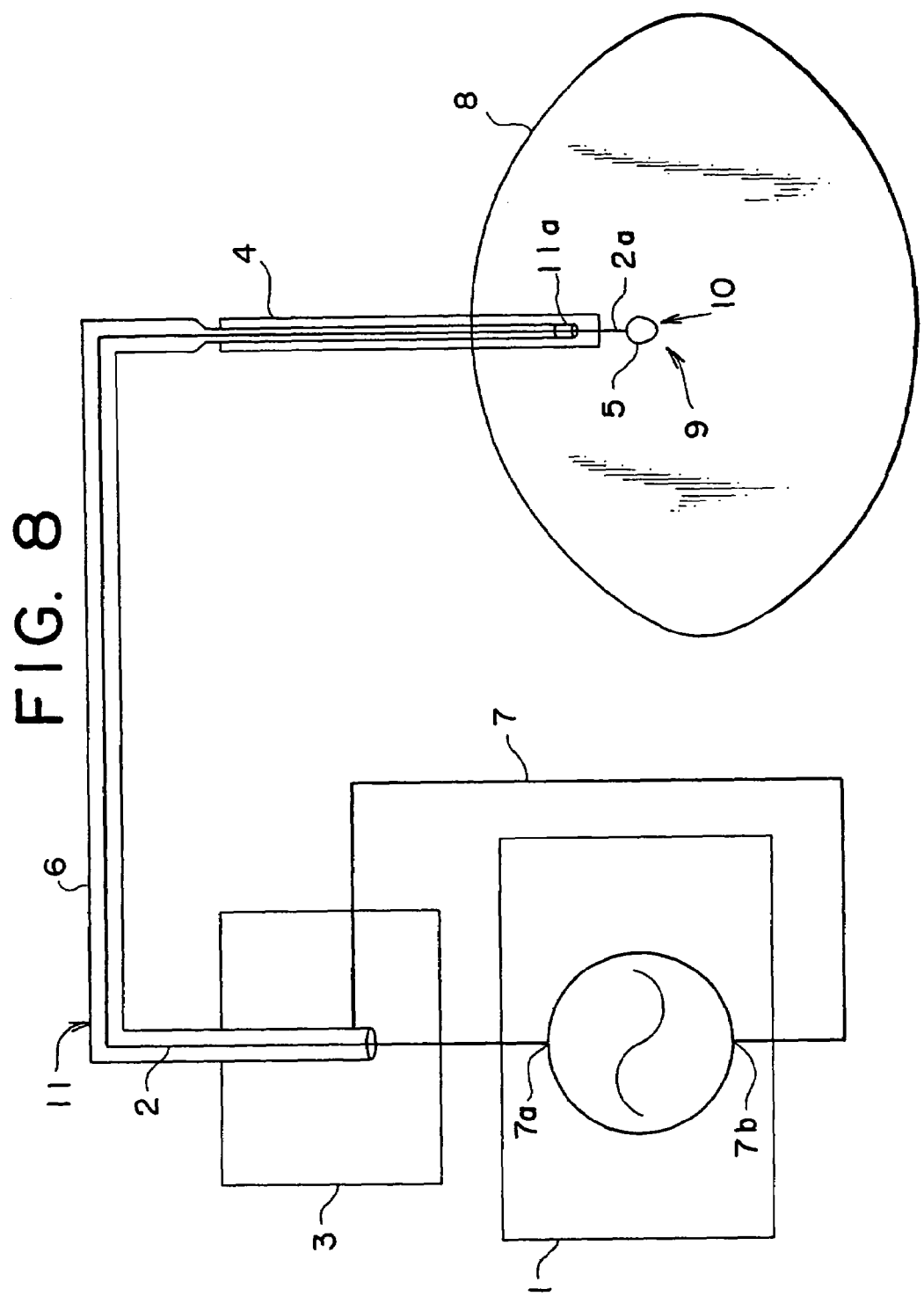
FIG. 8 is a schematic block diagram of a conventional apparatus for treating a biological tissue.
Figure 9:
FIG. 9 is a side view of a conventional electrode rod for treating a biological tissue.
Figure 10:
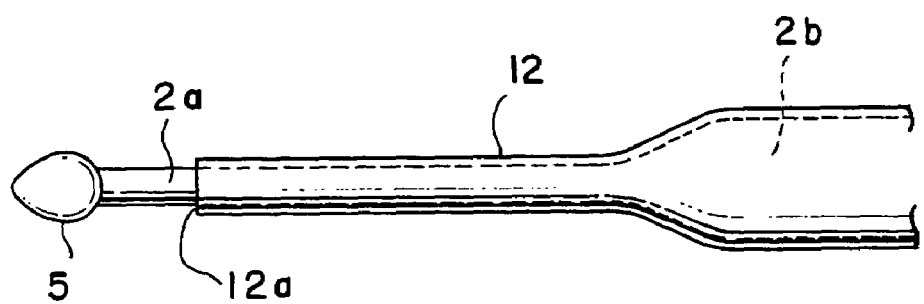
FIG. 10 is an enlarged side view of the tip of the electrode rod in FIG. 9.

In a sixth embodiment of the invention, an electromagnetic wave irradiating electrode 13e is formed in the shape of a knife, as shown in FIG. 7. In this case, the advantage resulting from the needle-shaped electrode 13a shown in FIG. 3 and that resulting from the blade-shaped electrode 13b shown in FIG. 4 can be obtained by the electrode 13e.

The structural parts shown in FIGS. 3 to 7 other than the electromagnetic wave irradiating electrodes 13a, 13b, 13c, 13d and 13e in the electrode rods for treating a biological tissue shown in the respective embodiments of the invention can be constituted such that they are completely the same as those other than the electromagnetic wave irradiating electrode 13 in the electrode rod for treating a biological tissue according to the first embodiment shown in FIGS. 1 and 2.

In the electrode rod for treating a biological tissue according to each embodiment of the invention, the diameter of a small metal core wire 14 should be determined 0.7 mm, and the length and outside diameter of the heat resisting non-metallic short tube 15 should be determined 3 mm and 1.1 mm, respectively. Since the heat resisting coating layers 16 and 16a are produced from tetrafluoroethylene, the electrode rod can be used with ease, and in particular, can be most suitably used for carrying out the operation of a brain at a diseased part inside a cranium.

In the above embodiments according to the invention, ceramic is used for the material of the heat resisting non-metallic short tube 15, so that the surface of the metal core wire 14 connected to the root part of the electrodes 13 and 13a–13e is thermally shielded, thereby making it possible to accurately carry out such a treatment of a biological tissue such as incision or the like using the electrode itself.

If, moreover, polyimide is used for the material of the heat resisting non-metallic short tube 15, an effect similar to that in the case of ceramic material can be obtained. Furthermore, the plastic material of polyimide provides an excellent workability in machining, thereby enabling the production cost to be reduced.

As described above in detail, the electrode rod for treating a biological tissue according to the invention provides the following advantages:

(1) The heat resisting non-metallic short tube which is mounted onto the outer periphery of the small diameter metal core wire connected to the electromagnetic wave irradiating electrode, covers the root of the electromagnetic wave irradiating electrode at the tip of the core wire, so that the exposure of the core wire the electrode at an extremely high temperature is suppressed in the state of operation, thereby making it possible to properly carry out the treatment of the biological tissue, such as incision or the like using the electrode. In this case, the heat resisting short tube is loosely mounted onto the small diameter core wire, so that no crack appears in the short tube even if the diameter of the core wire is increased by the thermal expansion. Moreover, the short tube is fixed by the heat resisting coating layer on the core wire, thereby enabling any movement of the short tube to be suppressed. Furthermore, a surgeon is able to bend such a small diameter core wire, thereby enabling a proper treatment to be carried out in accordance with the shape of the diseased part of the biological tissue.

(2) Since the electromagnetic wave irradiating electrode is formed in the shape of a ball, it can be properly used for dissipating the biological tissue due to the evaporation. In particular, the ball-shaped electrode is in contact with a larger area of the biological tissue, and the dissipation due to evaporation gradually takes place. Accordingly, the coagulation area due to the thermal conduction is increased, thereby enabling the ability in the arresting of bleeding to be enhanced.

(3) Since the electromagnetic wave irradiating electrode is formed in the shape of a needle, it can be properly used for incising the biological tissue. In particular, a decreased contact area of the needle-shaped electrode with the biological tissue allows the heat diffusion to be suppressed and makes it possible to carry out a sharp incision. As a result, the part in the vicinity of nerve where the heat diffusion is to be suppressed can be restricted using the tip of needle.

(4) Since the electromagnetic wave irradiating electrode is formed in the shape of a blade, the contact area of the electrode with the biological tissue is increased so that it is properly used for incising the biological tissue in which the incision is accompanied with the coagulation due to the thermal conduction.

(5) Since the electromagnetic wave irradiating electrode is formed in the shape of a ring, it can be properly used for excising a tissue providing a relatively small amount of bleeding at a wider area. In this case, a decreased contact area of the electrode with the biological tissue causes the thermal coagulation to be suppressed.

(6) Since the electromagnetic wave irradiating electrode is formed in the shape of a sickle, the biological tissue can be excised in a wider area, as similarly to the case of the ring-shaped electrode. However, an increased contact area of the electrode with the biological tissue provides the thermal coagulation more or less to some extent, and the dissipation due to the evaporation in the curved surface can also be carried out with the curved area at the tip of the electrode.

(7) Since the electromagnetic wave irradiating electrode is formed in the shape of a knife, the advantage resulting from the needle-shaped electrode 13a shown in FIG. 3 and that resulting from the blade-shaped electrode 13b shown in FIG. 4 can be obtained by the electrode 13e.

(8) The electromagnetic wave irradiating electrode is designed in such a way that the diameter of the small diameter metal core wire is 0.7 mm, the length and the outside diameter of the heat resisting non-metallic short tube are 3 mm and 1.1 mm, respectively, and the heat resisting coating layer is produced from tetrafluoroethylene. Accordingly, a surgeon can properly operate the diseased part of a patient by selecting the diameter of the small diameter metal core wire or the like and by bending the small diameter metal core wire in accordance with the shape of the diseased part.

(9) Since the material of the heat resisting non-metallic short tube is ceramic, the metal core wire connected to the electrode at the root can be thermally shielded in a proper manner, thereby making it possible to properly incise the biological tissue with the electrode itself

(10) Since the material of the heat resisting non-metallic short tube is polyimide, not only an effect similar to that in the case of ceramic, but also a workability of machining can be obtained with a reduced cost due to the plastic property of polyimide.

What is claimed is:

1. An electrode rod for treating a biological tissue comprising:
    a metal core wire having a given diameter and being capable of being used in a predetermined bent shape;
    an electromagnetic wave irradiating electrode connected at a root thereof to an end tip of the metal core wire;
    a heat resisting non-metallic short tube loosely mounted onto the outer periphery of said metal core wire so as to cover the root of said electromagnetic wave irradiating electrode;
    a first heat resisting coating layer coating the outer periphery of said short tube at the distal end thereof with respect to said electromagnetic wave irradiating electrode and coating the outer periphery of said metal core wire to fix said short tube;
    a rod-shaped rigid metal core wire having a relatively larger diameter than the given diameter of the metal core wire, said rigid metal core wire being integrally connected to said metal core wire; and
    a second heat resisting coating layer integrally connected to said first heat resisting coating layer and coating the outer periphery of said rod-shaped rigid metal core wire, except the outer periphery of a metallic surface at the proximal end thereof.

2. An electrode rod for treating a biological tissue according to claim 1, wherein said electromagnetic wave irradiating electrode is formed in the shape of a ball.

3. An electrode rod for treating a biological tissue according to according to claim 2, wherein the material of said heat resisting non-metallic short tube is ceramic.

4. An electrode rod for treating a biological tissue according to according to claim 2, wherein the material of said heat resisting non-metallic short tube is polyimide.

5. An electrode rod for treating a biological tissue according to claim 1, wherein said electromagnetic wave irradiating electrode is formed in the shape of a needle.

6. An electrode rod for treating a biological tissue according to claim 1, wherein said electromagnetic wave irradiating electrode is formed in the shape of a blade.

7. An electrode rod for treating a biological tissue according to claim 1, wherein said electromagnetic wave irradiating electrode is formed in the shape of a ring.

8. An electrode rod for treating a biological tissue according to claim 1, wherein said electromagnetic wave irradiating electrode is formed in the shape of a sickle.

9. An electrode rod for treating a biological tissue according to claim 1, wherein said electromagnetic wave irradiating electrode is formed in the shape of a knife.

10. An electrode rod for treating a biological tissue according to claim 9, wherein the material of said heat resisting non-metallic short tube is ceramic.

11. An electrode rod for treating a biological tissue according to claim 9, wherein the material of said heat resisting non-metallic short tube is polyimide.

12. An electrode rod for treating a biological tissue according to any one of claims 1–9, wherein the diameter of said small diameter metal core wire is 0.7 mm, wherein the length and the outside diameter of said heat resisting non-metallic short tube are 3 mm and 1.1 mm, respectively and wherein said first and second heat resisting coating layers are formed from tetrafluoroethylene.

13. An electrode rod for treating a biological tissue according to according to claim 1, wherein the material of said heat resisting non-metallic short tube is ceramic.

14. An electrode rod for treating a biological tissue according to according to claim 1, wherein the material of said heat resisting non-metallic short tube is polyimide.

* * * * *